United States Patent
Linder et al.

(10) Patent No.: US 8,380,539 B2
(45) Date of Patent: Feb. 19, 2013

(54) PERSONALIZED MEDICINE MANAGEMENT SOFTWARE

(75) Inventors: Mark W. Linder, Louisville, KY (US); Roland Valdes, Jr., Simpsonville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 146 days.

(21) Appl. No.: 12/300,104

(22) PCT Filed: May 8, 2007

(86) PCT No.: PCT/US2007/011033
§ 371 (c)(1),
(2), (4) Date: Jan. 19, 2009

(87) PCT Pub. No.: WO2007/133506
PCT Pub. Date: Nov. 22, 2007

(65) Prior Publication Data
US 2009/0138286 A1    May 28, 2009

Related U.S. Application Data

(60) Provisional application No. 60/798,855, filed on May 9, 2006, provisional application No. 60/859,803, filed on Nov. 17, 2006.

(51) Int. Cl.
*G06Q 50/00* (2012.01)
(52) U.S. Cl. .............................................. 705/3; 705/2
(58) Field of Classification Search ................... 705/2, 3; 600/300; 435/6
See application file for complete search history.

(56) References Cited

U.S. PATENT DOCUMENTS

| | | | |
|---|---|---|---|
| 5,833,599 A | * | 11/1998 | Schrier et al. ................. 600/300 |
| 6,081,786 A | * | 6/2000 | Barry et al. ........................ 705/3 |
| 6,450,956 B1 | * | 9/2002 | Rappaport et al. ............ 600/300 |

(Continued)

OTHER PUBLICATIONS

Mushiroda et al., Association of VKORC1 and CYP2C9 polymorphisms with warfarin dose requirements in Japanese patients, 2006, J Hum Genet, 51:249-253.*

(Continued)

*Primary Examiner* — Gerald J. O'Connor
*Assistant Examiner* — Jonathan K Ng
(74) *Attorney, Agent, or Firm* — Greer, Burns & Crain Ltd.

(57) ABSTRACT

The invention provides personalized medicine management software for determining a series of recommended doses of a medication for a patient. The software contains code to receive information regarding a combination of at least one genetic factor and personal attributes for the patient that are predictive of the patient's reaction to a series of doses of the medication. Using a predictive mathematical model specific to the medication, the code calculates the series of recommended doses specific to the patient's genetic factor and personal attributes and specific to the medication. The series of recommended doses is outputted. In preferred embodiments, the output is the form of an interactive display. The interactive display permits a user, typically a health care professional, to input actual doses and actual patient responses. The subsequent series of recommended doses is preferably then adjusted, in real time, to account for the actual doses and actual patient responses.

8 Claims, 4 Drawing Sheets

U.S. PATENT DOCUMENTS

| | | | |
|---|---|---|---|
| 7,445,896 B2 * | 11/2008 | Rieder et al. | 435/6 |
| 7,461,006 B2 * | 12/2008 | Gogolak | 705/2 |
| 7,546,285 B1 * | 6/2009 | Baker, Jr. | 1/1 |
| 2002/0076774 A1 * | 6/2002 | Yan et al. | 435/183 |
| 2004/0084867 A1 | 5/2004 | Leyland-Jones | |
| 2004/0093331 A1 * | 5/2004 | Garner et al. | 707/3 |
| 2004/0193446 A1 * | 9/2004 | Mayer et al. | 705/2 |
| 2005/0203773 A1 | 9/2005 | Soto et al. | |
| 2005/0260549 A1 * | 11/2005 | Feierstein et al. | 434/236 |
| 2006/0017563 A1 | 1/2006 | Rosenfeld et al. | |
| 2006/0084070 A1 | 4/2006 | Rieder et al. | |
| 2006/0166239 A1 * | 7/2006 | Chen et al. | 435/6 |
| 2006/0280786 A1 * | 12/2006 | Rabinow et al. | 424/450 |
| 2007/0003931 A1 * | 1/2007 | Mrazek et al. | 435/6 |

OTHER PUBLICATIONS

Yin et al., Warfarin dose and the pharmacogenomics of CYP2C9 and VKORC1—Rationale and perspectives, Aug. 2006, Thrombosis Research vol. 120 Issue 1 2007, 1-10.*

Pharmacokinetic Overview—D. McAuley (http://web.archive.org/web/20060118072914/http://www.globalrph.com/kinetics.htm#Calculate Predicted Peak and Trough). Retreived on Jan. 18, 2006.* www.collectivemed.com/software.shtml.

www.hospira.com/Products/HospiraMedNetSoftware.aspx.

www.nexdose.com/features/pc_interface.htm.

hsc.utoledo.edu/lib/education/pdanurssoftware.pdf.

* cited by examiner

FIG. 1B

PERSONALIZED MEDICINE MANAGEMENT SOFTWARE

PRIORITY CLAIM

This application claims priority under 35 U.S.C. §119 from prior provisional application Ser. Nos. 60/798,855, which was filed on May 9, 2006 and 60/859,803, which was filed Nov. 17, 2006.

STATEMENT OF GOVERNMENT INTEREST

This invention was made with Government support under AA014235 awarded by the National Institutes of Health. The Government has certain rights in the invention.

TECHNICAL FIELD

A field of the invention is the medical field. The invention provides personalized medicine management software.

BACKGROUND OF INVENTION

In order to achieve the desired efficacy for certain pharmaceutical medicines, there exists a persistent and ongoing need for first selecting the correct medications for addressing a particular disease, and then titrating those medications over time to make sure an individual is receiving the proper dose. Not only is this problem created by the nature of a particular disease, it might also be compounded by a patient's particular response to a particular medicine, where the latter is attributable to a host of factors, such as the patient's unique genetic composition, gender, degree of affliction, diet, weight, smoking status, or other factors that might mitigate efficacy of a specific medicine. Accordingly, the titration necessary to optimize efficacy is highly dependent on the individual, and often times, clinical plans are too generic or overbroad, and fail to sufficiently account for individual responses to a particular dosage.

There are a number of studies that have shown how the level of drug in a patient's blood stream varies for the same dosing depending upon the individual patient's genetic composition and personal attributes. Various mathematical models have been established by studies and can predict bloodstream concentrations of particular drugs in response to particular dosing in individual patients based upon factors relating to the patient's genetic factors and personal attributes.

Despite the availability of accurate models in the art to evaluate a patient's reaction to dosing based upon genetic factors and personal attributes, actual practice remains rooted in trial and error aided by basic information and time honored dosing strategies. Doctors can consult, for example, the dosage recommendations and induction protocols provided by pharmaceutical manufacturers. Common induction protocols are also favored, such as, in the example of the anticoagulant warfarin, the popular "10-7-5" protocol in which dosage begins at 10 mg, moves to 7 mg and then down to 5 mg. Doctors administering medicine are unlikely to consult any models or conduct any calculations based upon genetics and personal attributes, and a tool is not provided to aid dosing. Blood tests, such as the PT/INR test to check blood coagulation, are conducted frequently until a stable level is achieved. Doctors adjust dosage in response to monitored patient response. The adjustments selected and the timing of the adjustments can vary significantly from doctor to doctor.

As such, patients frequently receive either too much or too little of a needed drug as doctors and clinicians "over-steer" in an attempt to administer or prescribe the correct dosage. Adverse drug reactions are a leading cause of death in the United States, with over 100,000 deaths per year and over 2.2 million hospitalizations per year.

For example, in anticoagulation clinics, patients may be administered warfarin in an attempt to regulate over-coagulation caused by various thromboembolic diseases. Warfarin is the most commonly prescribed anticoagulant, but unfortunately, its complex dose-response relationship presents an ongoing challenge to its safe and effective use. Typically, patients visit an anticoagulation clinic on a specific schedule, such as every 24 days, to have their status monitored and have dosage adjustments made, if necessary, to the patient's "maintenance dose." However, the pharmacological response to warfarin is delayed, making it difficult for a doctor to determine whether the adjustment has accurately corrected the dosage, or has overcorrected the dosage to the point where the patient will end up over-anticoagulating or sub-anticoagulating.

SUMMARY OF THE INVENTION

The invention provides personalized medicine management software for determining a series of recommended doses of a medication for a patient. The software contains code to receive information regarding a combination of at least one genetic factor and personal attributes for the patient that are predictive of the patient's reaction to a series of doses of the medication. Using a predictive mathematical model specific to the medication, the code calculates the series of recommended doses specific to the patient's genetic factor and personal attributes and specific to the medication. The series of recommended doses is outputted. In preferred embodiments, the output is the form of, an interactive display. The interactive display permits a user, typically a health care professional, to input actual doses and actual patient responses. The subsequent series of recommended doses is preferably then adjusted, in real time, to account for the actual doses and actual patient responses.

BRIEF DESCRIPTION OF THE DRAWINGS

FIGS. 1A and 1B illustrate a preferred embodiment graphical user interface for personalized medicine management software and together show an interactive response of the software of a preferred embodiment;

DETAILED DESCRIPTION OF THE PREFERRED EMBODIMENTS

Figure 1A:
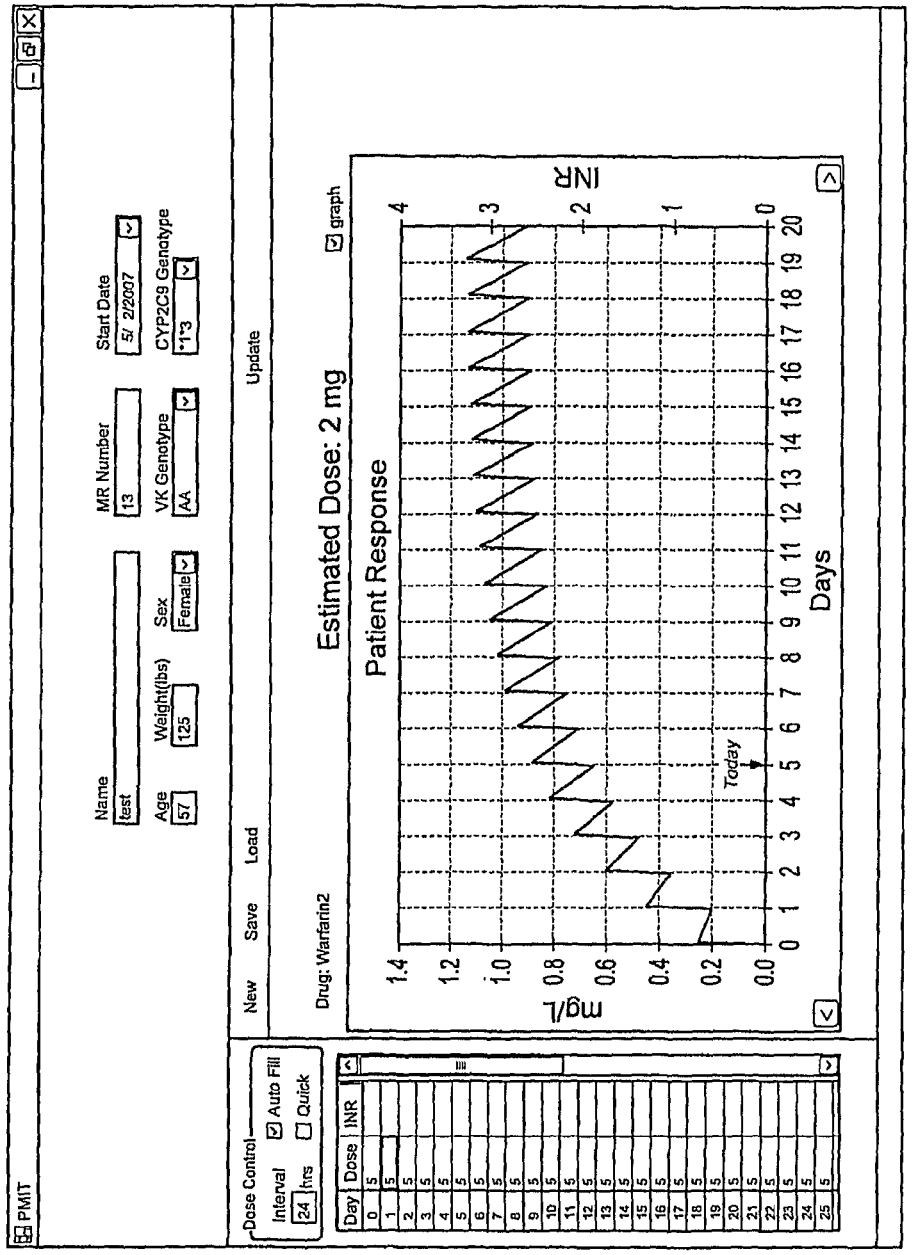

The invention provides personalized medicine management software for determining a series of recommended doses of a medication for a patient. The software contains code to receive information regarding a combination of at least one genetic factor and personal attributes for the patient that are predictive of the patient's reaction to a series of doses of the medication. Using a predictive mathematical model specific to the medication, the code calculates the series of recommended doses specific to the patient's genetic factor and personal attributes and specific to the medication. The series of recommended doses is outputted. In preferred embodiments, the output is the form of an interactive display. The interactive display permits a user, typically a health care professional, to input actual doses and actual patient responses. The subsequent series of recommended doses is preferably then adjusted, in real time, to account for the actual doses and actual patient responses.

The genetic factor and personal attributes received by the software of the invention preferably include genotype and one or more of the patient's gender, height, weight, age, co-medications, ingested materials, and similar factors. A graphical user interface preferably outputs the series of recommended doses and, for each one of the series of recommended doses, the patient's response to the series of doses. A tabular format is preferred for the recommended doses and the predicted patient response. Additional, in preferred embodiments, patient response is also graphically represented.

Preferred embodiment software also conducts traditional record keeping functions. Preferably, data is maintained to record and store, separately for each patient and for each medication, the series of recommended doses and the patient's predicted responses. The software can also maintain data concerning inputted actual doses and actual patient responses.

Software of the invention makes use of mathematical models developed from studies particular to the medication. Various mathematical models are available and have been computed as genomic data becomes better understood and more widely studied. Mathematical models for medications that consider genetic factors and personal attributes are an area of ongoing research, and new models can be used to practice the invention as such models become established.

A particular preferred embodiment of the invention that concerns medications administered to control patient blood coagulation applies a preferred novel model for predicting patient response to medication. In preferred embodiments a mathematical regression model determines the patient's optimal series of recommended doses for a particular medication.

Software of the invention can be implemented in various systems. It can be implemented in local area networks, wide area networks, e.g., the Internet, or on individual computers. The software can be sold to individual or institutional users, or can be a subscription service, for example accessed through a secure web site. In preferred embodiments, personalized medicine management software is implemented on or accessible by mobile computing devices.

Software of the invention uses patient specific personal attributes and current data regarding genotype to guide dosing of difficult to manage therapeutic drugs. A preferred embodiment uses genetic factors and personal attribute information regarding warfarin, but the invention is also applicable to other drugs that can have their responses modeled mathematically with genetic factors and personal attributes. Particular contemplated examples include fluoxetine and atomoxetine. Additional examples in which ongoing titration is a concern include dilantin, glipizide, celebrex, and risperidone. The invention is particularly useful to personalize the management of drugs having a narrow therapeutic index and drugs where other measures to estimate drug exposure are not routinely applied.

Pharmacogenetics has an impact of drug selection and efficacy that cannot be understated. Pharmacogenetics impacts drug metabolism and drug effects in a relatively predictable manner, when the genetic underpinnings are determined. Thus, genotype influences phenotype, where the phenotype is drug metabolism and patient response to the drug. For example, it is known that S-warfarin is metabolized by CYP2C9, but that CYP2C9*2 and CYP2C9*3 are slow metabolizers, comparatively. Accordingly, patients having either the CYP2C9*2 and CYP2C9*3 genotypes will exhibit slower metabolism of warfarin. Similarly, variants of VKORC1 ("VKOR variants") influence the amount of this warfarin target protein and confer a 2.6 increased risk of bleeding. Together, variants of CYP2C9 and VKOR, and personal attributes such as age, and height can account for greater than 60% of the variability in maintenance dose requirements of warfarin. Correctly titrating dosages according to genetic factors and personal attributes can therefore drastically reduce adverse drug reactions.

Preferred embodiment software can be used to determine an optimal series of doses including initial and maintenance doses and in guiding individualized drug therapy. Preferred embodiment software determines the most appropriate dosing strategy for a patient and displays this treatment strategy in an easy to interpret and highly informative manner. The software implements a dynamic and interactive model that allows a practitioner to make highly informed decisions. Additionally, the model promotes patience and gives the practitioner visual reinforcement such that the practitioner is less inclined to prematurely over interpret the relationship between dosing and patient response.

Many dosing and monitoring strategies are improved by preferred embodiment software of the invention, as will be appreciated by artisans. Software of the invention can determine and provide a series of recommended doses to be given to a patient and can make dynamic, interactive adjustments based upon inputted data concerning actual dosages and measured patient responses. Peak concentrations of a drug after each dose can be estimated and provided by the software and adjust to inputted data in real-time. The trough concentration of a drug after each dose can also be estimated and provided. The dosing interval (in time) including variation in that time, can be estimated and provided, e.g., permitting a physician flexibility in the timing of particular doses. Preferred software of the invention can also estimate the time required to reach steady state in blood. Additionally, preferred embodiment tools can estimate time for accurate monitoring of drug concentration or physiologic response, which is only accurately measured at steady state.

In a particular preferred embodiment, multiple models can be applied to permit selection of different dosing strategies. For example, a standard dose series or a quick dose series can be selected. In the quick dose series, the fastest dose strategy is determined to get a patient's predicted response into the desired range.

Additionally, preferred embodiment software can provide appropriate required concentration at steady state for optimal physiologic response based on the genotype of the drug's receptor. This allows, for example, a physician to estimate, based upon particular dosing scheme; a target dose to maintain concentration for steady state based upon genotype (2C9 and VCOR for warfarin, for example). Also, preferred embodiment software of the invention corrects the individual patient's dosing parameters based on real-time feedback by modeling a patient response instead of trial and error using the patient.

Preferred embodiment software will now be discussed with respect to the drawings. The preferred embodiment software concerns medications for treating blood coagulation, and will be discussed with respect to a preferred mathematical model, but artisans will appreciate that the principles of the invention can be used for other medications and with other mathematical models. Various coding strategies and operating systems can be used to implement software of the invention. The principle operations of preferred embodiment software will be discussed with reference to the inputs, outputs, calculations and displays of a preferred embodiment. Coding of the software in any number of architectures and languages, and implementation of specific coding is within the skill of an ordinary artisan.

Figure 1B:
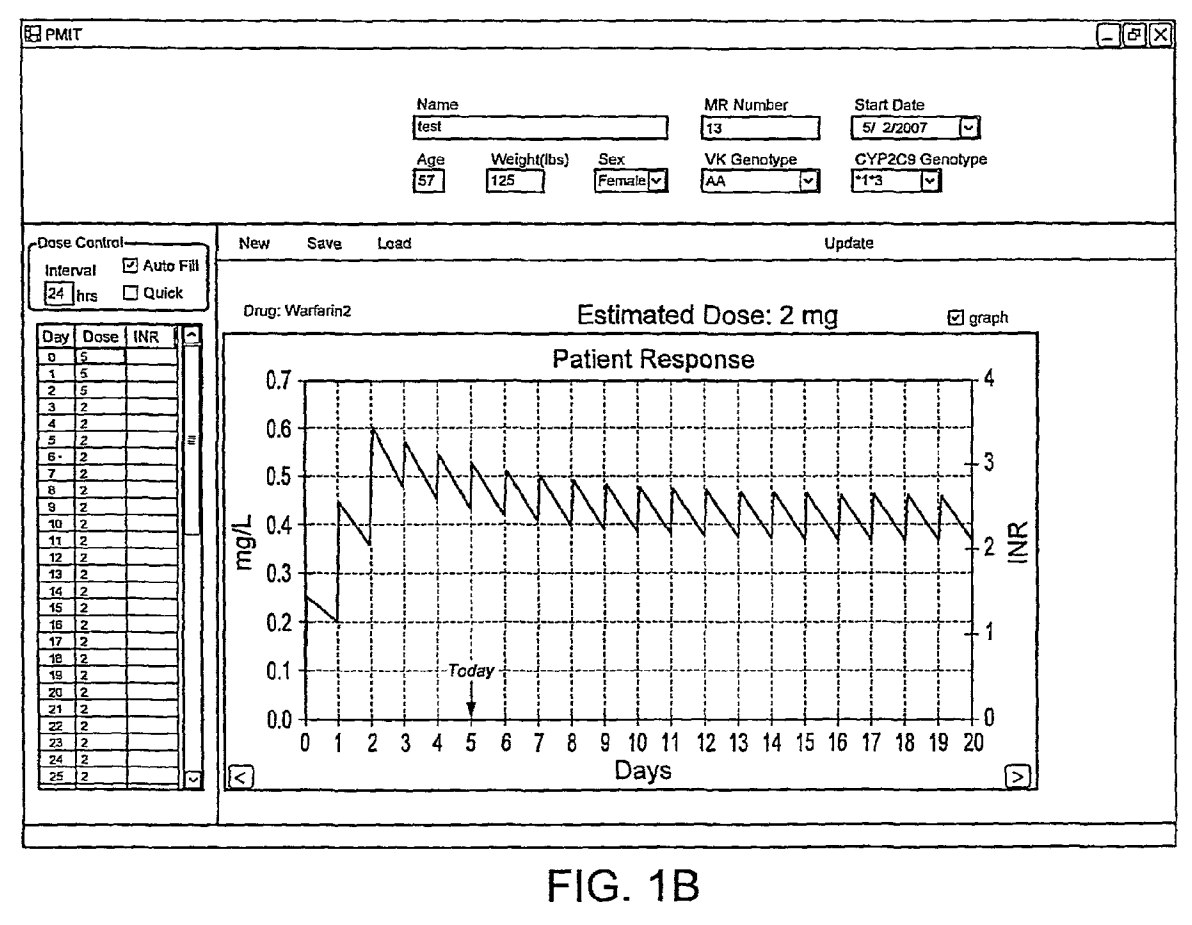

FIGS. 1A and 1B illustrate a preferred embodiment graphical user interface for personalized medicine management software and together show an interactive response of the software of a preferred embodiment. In both FIGS. 1A and 1B a graphical user interface aids the creation of patient files and the obtainment of a personalized strategy for management. Patient name, number, start date, age, weight, sex and two genetic factors are presented in separate entry fields, which in the case of the genetic factors is preferably a pull down menu specific to the medication. In FIGS. 1A and 1B, the medication being managed is warfarin, and the pull down genetic factors are for the VK and CYP2CP genotypes. Options are presented for creating a new patient file, saving the current patient file, loading a patient file, and updating the display. In a dose control section, an interval can be selected and auto fill and quick dose options are presented. In the tabular section that is based upon intervals, the dose and INR fields are interactive. The doses are auto filled to obtain a series of recommended doses for a particular patient, but those entries can be replaced with actual doses. The graph shows the patient response. In FIG. 1A, actual entries of 5 mg/day, which is the standard starting dose, were entered in the table, and this results in a predicted patient response of an overdose situation in which the plasma concentration of the drug is greater than 1.0 mg/L. Thus the practitioner is altered to the fact that the standard dose of 5 mg/d for this individual presents a risk of overdosage occurring on or about day 10 of therapy. In FIG. 1B, the model presents a series of recommended doses based on a standard induction protocol of 5 mg for the first 3 days followed by conversion to the estimated maintenance dose of 2 mg/d calculated based on the specific genetic and physical characteristics of the individual. Note in contrast to FIG. 1A, that the concentration of the medication at this dose is less then 0.5 mg/L which is a safe and effective concentration. In the table, actual INR can be entered, and the model will update, if necessary, the dosage to account for the response of the particular patient. In addition, the quick dose can be selected to present a model to get a patient to the desired therapeutic concentration as quickly as possible. The Quick Change Dose function, given a date and dose, calculates exactly how many mg of the drug are required for the Cmax to reach steady state in one dose. It does this by calculating a Cmin value from the previous doses by simulation. Then by solving the equations:

$$Cmax_{ss} = desiredDose*(s*f/vd)/(1-10^{(-0.3*24/t1/2)})$$

$$Cmax = Cmin*10^{(-0.3*Tpeak/t1/2)} + dose*(s*f/vd)$$

$$Cmax_{ss} = Cmax = Cmin*10^{(-0.3*Tpeak/t1/2)} + immediateDose*(s*f/vd)$$

$$Immediate\ Dose = (Cmax_{ss} - Cmin*10^{(-0.3*Tpeak/t1/2)})/(s*f/vd)$$

This immediate dose then is bounded between 0 and a realistic maximum dosage (e.g. 10 mg/d for warfarin). Bounding protects the patient from overdosing, or negative doses. However now it could take more than one dose to reach the steady-state. The program then sets the given day to the bounded immediate dose, and repeats the function for the next day and so on.

As can be seen from FIGS. 1A and 1B, embodiments of the invention are particularly advantageous in that they provide a doctor or other medical clinician with a calculation tool for selecting which medicines to administer as well as accurately and optimally titrating medicine dosages by accounting for various important individual factors, including pharmacogenetic influence, and personal attributes such as gender, height and weight, to name a few exemplary factors. Embodiments take into account real-time information as well as a patient's historical data, and are thus dynamic and responsive to a patient's unique physiology.

Generally speaking, preferred embodiments of the invention can make use include a variety of established or newly developed mathematical models determining an individual patient's optimal dosing strategy and guiding individualized drug therapy. Among other factors that may be considered, embodiments of the invention takes into account pharmacogenetic factors, and personal attributes such as gender, smoking status, height, weight as well as actual patient response to the medicine, and/or other relevant characteristics of an individual patient, and subsequently determines the most appropriate dosing and monitoring strategy for that patient.

Software of embodiments of the invention can provide a series of recommended doses at any point in drug therapy for an individual patient. Preferably, a series of recommended doses includes an initial dose and subsequent doses to get to a maintenance dose level. However, a patient can also be prescribed a first dose for a period of time, such as four days for example, where the first dose is determined based on conventional criteria. This can be a place of treatment that is not implementing software of the invention, for example. The software can then be applied, such as at a clinic for monitoring patients on drug therapy. The software provides a visual representation of the patient's current treatment status, which can then be used to make future dosing and monitoring decisions. The real-time results of the patient's current treatment status and response to the medicine based on the recent dosing history and such influences as genotype, and personal attributes such as gender, height, weight, smoking status, and others, are provided to the software program, which then calculates a patient's future optimal dosing strategy.

Embodiments are particularly advantageous in that the dosing and treatment strategy may be displayed in an easy to interpret and highly informative manner, creating a visible guideline for both patient and doctor. In addition to clearly alerting the doctor to the potential need to adjust dose, anomalies may indicate an issue that the doctor may wish to address with the patient. For example, where an otherwise regular curve begins to change where all identified variables have remained the same, the doctor may discuss dietary or other lifestyle changes the patient may have undertaken. Similarly, a change in the graph following such a dietary or lifestyle change provides valuable visual evidence to the patient that the diet or other lifestyle change is actually impacting the patient's successful treatment.

More particularly, embodiments of the invention include one or more patient-specific files that display a drug management strategy, which, based on statistical data is most likely to yield optimal drug response in that particular patient. The patient's file is then routinely updated with the medicine dosages and other care actually received by the patient. A graphical patient history may then be created, which, in conjunction with the predictive value of the invention, provides clinicians a unique advantage for the individualized care of their patients.

In an exemplary embodiment, a regression model predicts a patient's proper series of recommended doses. A patient's data file will include two sub-files, where a first sub-file is completed by the model to indicate the patient's theoretical optimal dose. The first sub-file preferably includes a uniform dose for the first four days, and then adjusts to an individualized dose on a fifth day. A second sub-file reflects actual patient data, which the practitioner enters based on real-time information, such as the doses actually administered over the first four days.

Example Interactive Dosing Strategy

Figure 2:
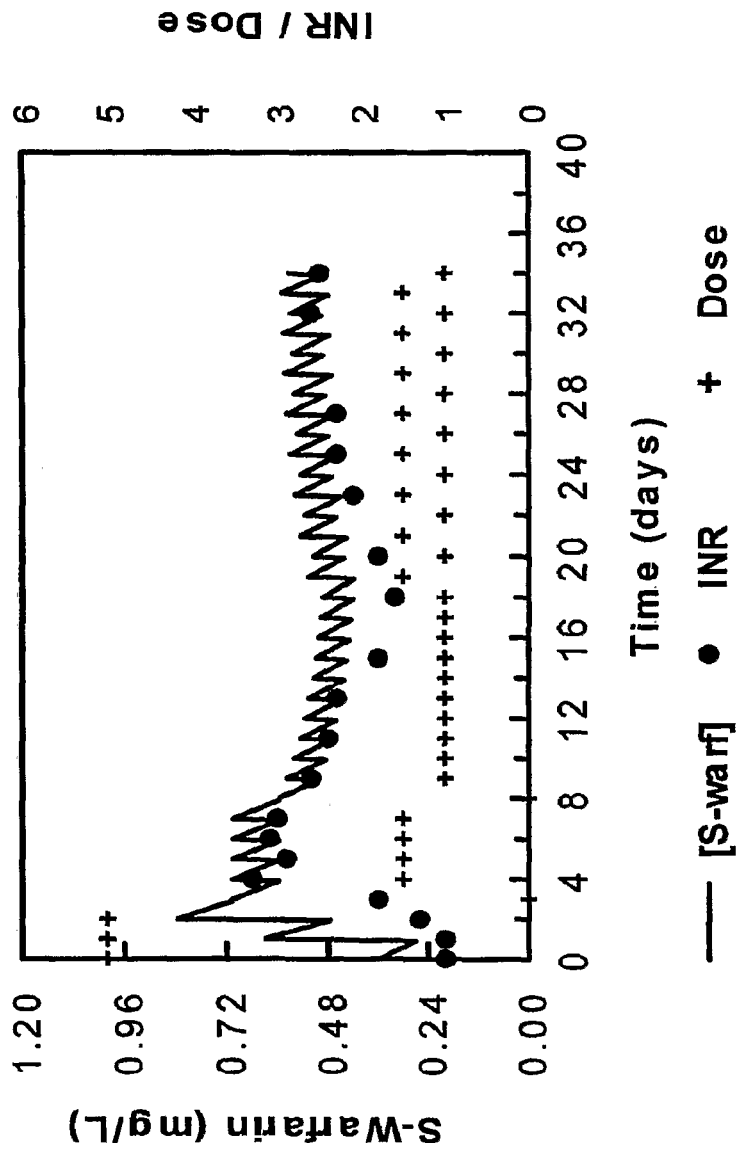
FIG. 2 illustrates a recommended maintenance dose for a female subject having the CYP2C9*1/*3 and VKORC1 G/G genotype.

FIG. 2 illustrates a recommended maintenance dose for a female subject having the CYP2C9*1/*3 and VKORC1 G/G genotype. The recommended maintenance dose is 1.5 mg/day. The example is illustrative of at least two important factors in evaluating the efficacy of warfarin. One point is that females typically require less medicine than do men, and another is that the pharmacogenetic impact of the two genotypes CYP2C9 and VKOR has important implications on maintenance dose as well.

With reference to FIG. 2, the predicted maintenance dose for a female subject having the CYP2C9*1/*3 and VKORC1 G/G genotype is 1.5 mg/d. This model would illustrate that an optimal dosing strategy for this individual would be to initiate standard therapy of 5 mg/d for the first 3 dosages. The dose on day 4 would be held (no dose on day 4) and the target maintenance dose would be administered on day 5 and continued. This is predicted to maintain the S-warfarin plasma concentrations at the projected therapeutic concentration, which is based in part on the VKORC1 genotype.

In the event that the INR or drug concentration does not mirror the anticipated response, software of the invention allows for the care giver to enter in an alternative dosing strategy and visualize the anticipated change in therapy.

For example, assume that the INR remains close to 3 on days 6 and 7 of therapy and the practitioner chooses to lower the dose on day 8 to 1 mg/day. The model responds and demonstrates how the S-warfarin plasma concentration begins to decline. Modeling can show that INR drops through the target range of 2 to 3 and is sub-therapeutic at the time when the 1 mg/d dosing is reaching steady-state, approximately day 18. As illustrated in FIG. 2, the practitioner can predictably make an adjustment that increases the dose by alternating 1.5 mg/d with 1.0 mg/d dosing, the plasma S-warfarin concentration climbs slightly and at steady-state yields an INR measurement which is reproducibly within the target range.

The interactive nature of the software allows the practitioner to make highly informed decisions. The modeling and graphical display through the graphical user interface promotes patience and gives the practitioner visual reinforcement not to prematurely over interpret the relationship between dosing and response. By day 36 in the graphical display shown in FIG. 2, the practitioner can see that the blood concentrations of S-warfarin have stabilized at the current dose rate and that the INR measurements have consistently demonstrated optimized therapy. At this time, the practitioner can in confidence, increase the time interval between monitoring the INR.

Example Modeling and Software Data Structure

Figure 3:
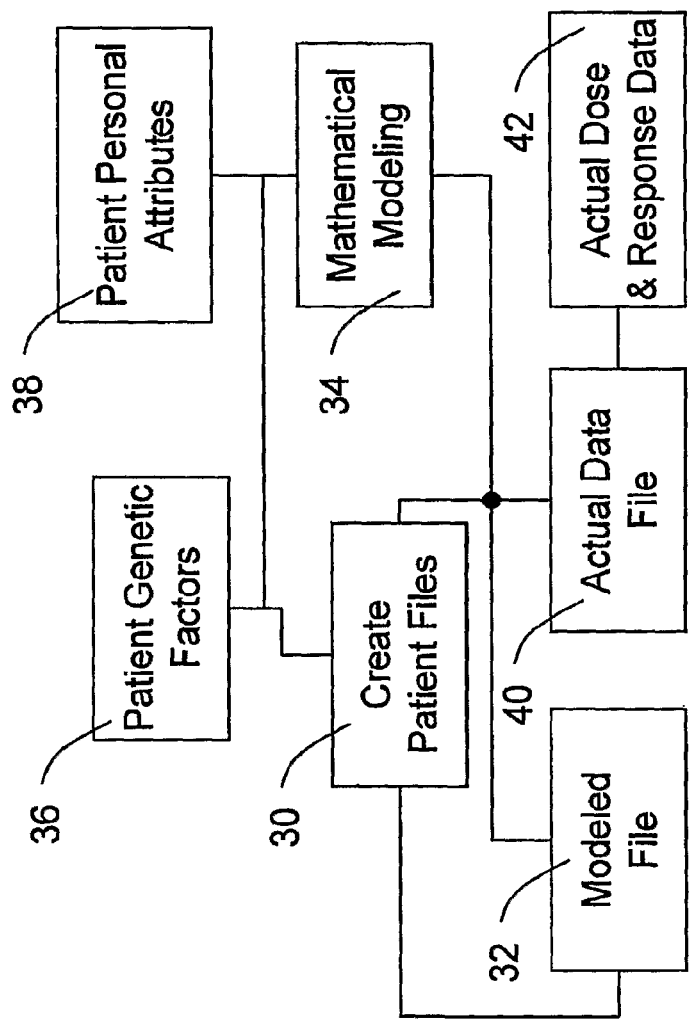
FIG. 3 shows schematic diagram of information stored and operations performed by preferred embodiment software.

FIG. 3 shows schematic diagram of information stored and operations performed by preferred embodiment software. In a preferred embodiment, the software creates 30 two files for each patient. One file is a modeled data file 32 that includes data illustrated by the FIG. 2 graph, which depicts a theoretical optimal dosing strategy based on the model employed by the software. Specifically, a mathematical model 34 receives data regarding the patients genetic factor(s) 36 and personal attributes 38. Another file maintained by the software is an actual data file 40 that maintains data that can be used to generate a real-time plot of the patient's actual dosage and patient response data 42 entered.

The patient genetic factors 36 can be determined from a sample of blood. For example, the blood sample can be used to determine the CYP2C9 and VKORC1 genotypes. Patient personal attributes 38 can include, for example: Age, Weight, Sex, Smoking status, Medication A, Medication B (medications that may interact with the medication that is being modeled by the model 34).

The model in an example uses the equations as shown below, and permits calculation of the dose (D)) that will eventually be required to maintain anticoagulation of the patient.

| Predictor(s) | Regression Equation | Model P-value | $R^2$ |
|---|---|---|---|
| Age | log(D) = 2.870 − 0.020 (Age) | 0.0003 | 0.18 |
| Sex | log(D) = 1.276 + 0.415 (Sex) | 0.0024 | 0.13 |
| Weight | log(D) = 0.298 + 0.006 (Weight) | <0.0001 | 0.28 |
| VK3673 | log(D) = 1.349 − 0.426 (VK3673 − M) + 0.426 (VK3673 − W) | 0.0001 | 0.27 |
| 2C9* | log(D) = 1.659 − 0.248 (2C9*2) − 0.625 (2C9*3) | 0.0003 | 0.22 |
| Full Model (All variables) | log(D) = 1.35 − 0.008 (Age) + 0.116 (Sex) + 0.004 (Weight) − 0376 (VK3673 − M) + 0.271 (VK3673 − W) − 0.307 (2C9*2) − 0318 (2C9*3) | <0.0001 | 0.61 |

Another parameter that can be estimated, for example, is the target plasma concentration required during therapy. This can be based on the VKORC1 genotype

VKORC1

GG: 0.73 ug/mL ±0.33 (n−29)

GA: 0.54 ug/mL ±0.21 (n−21)

AA: 0.48 ug/mL ±0.04 (n−5)

Target concentrations can be displayed in a graph on the graphical user interface, with one color of line, for example green. The change in drug concentration following each dose and at each time during the dosage interval are depicted in a graphical user interface. The changes in drug concentration for a given dose and over time is a function of the individual patients drug clearance rate that is derived based on genotype and other physical characteristics of the patient. The change in drug concentration are then provided in a graphical user interface and allows for estimation of time to reach steady-state, alters the clinician to overdose or under dosing and allows for modeling of alternative dosing strategies in order to determine the most appropriate dosing and monitoring strategy for that given patient. Changes in drug concentration over time are calculated, for example, using the two equations:

$$C_{max} = Dose * (s*f/vd)/(1-10^{(-0.3*24/t1/2)})$$

$$C_{min} = C_{max} * 10^{(-0.3*Tpeak/t1/2)}$$

Where the t1/2 is determined based on the individuals CYP2C9 genotype and other physical characteristics including age and gender and Cmin at steady-state is estimated from the individuals VKOR C1 genotype.

Many programs and coding strategies can be used to manage the data in the FIG. 3 example and similar embodiments of the invention and to produce the graphical user display example in FIG. 1. Simple spreadsheet programs, e.g., Excel, for example, can calculate the concentrations at the beginning and end of each dosing cycle. Any graph generating program can use the data of the mathematical model to plot concentrations. Example outputs have been produced using Slidewrite.

Warfarin Dosing Model Development

Preferred embodiment personalized medicine management tools can be based upon currently known data, and artisans will appreciate that additional data can be developed. The invention includes a preferred model which was developed based upon a study and obtained data to predict warfarin doses based upon genetic variations of VKORC1 and CYP2C9 in addition to personal attributes.

In addition to the personal attributes of age, diet, body weight, concomitant medications, and race, recent studies have shown that both VKORC1 and CYP2C9 genetic variations are associated with variable warfarin dose requirements. Many published studies concerning the impact are available and can be used to develop different models.

Although genotypes of VKORC1 and CYP2C9 are two crucial genetic factors determining patients' warfarin dose requirements, age, gender, body weight, and other factors also play important roles. As has been demonstrated by others and confirmed in research conducted in testing the present invention, VKORC1 and CYP2C9 have a similar impact on warfarin dose requirements and genotyping both VKORC1 and CYP2C9 in conjunction with the patient's physical characteristics will help physicians and pharmacists estimate warfarin dose more precisely and thus improve the efficiency of the dosage titration process. The example multivariate math model presented above provides one tool for calculation of recommended doses and patient responses.

While various embodiments of the present invention have been shown and described, it should be understood that modifications, substitutions, and alternatives are apparent to one of ordinary skill in the art. Such modifications, substitutions, and alternatives can be made without departing from the spirit and scope of the invention, which should be determined from the appended claims.

Various features of the invention are set forth in the appended claims.

What is claimed is:

1. Personalized medicine management software stored on a non-transitory computer medium for causing a computer to determine a series of a recommended doses of an anticoagulant medication for a patient, the software containing code for causing a computer to conduct the following steps:

receiving information regarding a combination of the genotypes of VKORC1 and CYP2C9 and personal attributes for the patient that are predictive of the patient's reaction to a series of doses of the anticoagulant medication;

with a predictive mathematical model specific to the medication, calculating a series of recommended doses specific to the patient's at least one genetic factor and personal attributes specific to the medication, wherein the model predicts maintenance dose series based upon the patient's VKORC1 and CYP2C9 and a calculated clearance of the anticoagulant medication;

receiving actual dose and measured patient response data and adjusting the patient's calculated clearance of the medication based on CYP2C9 genotype and a target blood concentration required for optimal therapeutic response that is adjusted based on the VKORC1;

graphically displaying a representation of dosing and concentration, wherein the representation graphically represents time for blood concentrations of the anticoagulant medication to achieve or transition to a steady-state for a given dosing, and wherein the graphic dosing rate is changed in response to said step of receiving and wherein the graphical representation of anticoagulant medication concentrations in blood are plotted in conjunction with measured medication response to add temporal dimension to the interpretation of the medication response parameter; and wherein the representation that is graphically displayed includes overlays of anticoagulant medication concentration, measured medication response, and dosing over time and wherein the representation is updated in real time after said step of receiving.

2. The software of claim 1, wherein the measured medication response is INR.

3. The software of claim 2, further comprising a step of recording and storing, separately for each patient and for each anticoagulant medication, data concerning the anticoagulant medication concentration, INR and dosing over time.

4. The software of claim 1, wherein said step of calculating comprises applying a mathematical regression model to determine the patient's optimal series of recommended doses.

5. The software of claim 1, wherein the personal attributes of the patient are selected from the group consisting of gender, height, weight, age, race, co-medications, and ingested materials.

6. The software of claim 1, wherein the anticoagulant medication comprises warfarin.

7. The software of claim 1, wherein the mathematical model further estimates a target plasma concentration required during therapy.

8. The software of claim 7, wherein the plasma concentration is determined by the mathematical model based on the VKORC1 genotype.

* * * * *